United States Patent [19]

Antoon, Jr. et al.

[11] Patent Number: 5,628,732
[45] Date of Patent: May 13, 1997

[54] TROCAR WITH IMPROVED UNIVERSAL SEAL

[75] Inventors: Mitchell K. Antoon, Jr., Cincinnati, Ohio; Michael A. Murray, Bellevue, Ky.; Robert T. Alvarez, Carlsbad, Calif.

[73] Assignee: Ethicon Endo-Surgery, Inc., Cincinnati, Ohio

[21] Appl. No.: 588,850

[22] Filed: Jan. 19, 1996

[51] Int. Cl.⁶ ........................................... A61M 5/178
[52] U.S. Cl. ................................. 604/167; 604/256
[58] Field of Search ................................ 604/256, 167, 604/249, 264, 164, 158

[56] References Cited

U.S. PATENT DOCUMENTS

| 5,209,737 | 5/1993 | Richart et al. | 604/167 |
| 5,300,036 | 4/1994 | Mueller et al. | 604/167 |
| 5,308,336 | 5/1994 | Hart et al. | 604/167 |
| 5,338,307 | 8/1994 | Stephens et al. | 604/167 |
| 5,342,315 | 8/1994 | Rowe et al. | 604/167 |
| 5,385,553 | 1/1995 | Hart et al. | 604/167 |
| 5,395,342 | 3/1995 | Yoon | 604/167 |
| 5,407,433 | 4/1995 | Loomas | 604/167 |
| 5,411,483 | 5/1995 | Loomas et al. | 604/167 |
| 5,456,284 | 10/1995 | Ryan et al. | 604/256 X |
| 5,520,655 | 5/1996 | Davila et al. | 604/167 |
| 5,520,663 | 5/1996 | Patterson et al. | 604/256 |
| 5,562,632 | 10/1996 | Davila et al. | 604/167 |

*Primary Examiner*—John D. Yasko
*Attorney, Agent, or Firm*—Matthew S. Goodwin

[57] ABSTRACT

A trocar containing a universal seal for sealing against surgical instruments of varying diameter to maintain insufflation in the body cavity is disclosed. The universal seal has an elastomeric sealing component with a centrally located interior region containing an aperture, and a concentrically located sealing region. The sealing region is composed of an integral laminate having an overlaying layer co-molded with an underlying layer. The overlaying layer has a hardness between about 40 Shore A Durometer Scale and about 80 Shore D Durometer Scale. The underlying layer has a hardness between about 5 Shore A Durometer Scale and about 40 Shore A Durometer Scale. The co-molded laminate balances the properties of tear resistance and elasticity which are necessary for a working universal seal, and does so without the need for resilient legs or protectors to facilitate the opening of the aperture of the seal or to prevent tearing when instruments are inserted.

11 Claims, 9 Drawing Sheets

TROCAR WITH IMPROVED UNIVERSAL SEAL

BACKGROUND OF THE INVENTION

This invention relates to a surgical trocar for puncturing the body wall of a patient to provide access to a surgical site during endoscopic surgery. More specifically, it relates to a trocar incorporating a universal seal to minimize or prevent leakage of insufflation fluid from the surgical site through the trocar when instruments are inserted through the trocar.

A critical feature of a trocar is the design of the seal which prevents the passage of insufflation fluid through the trocar when instruments of varying sizes are inserted through it. During endoscopic surgery, the abdomen is insufflated with carbon dioxide to provide space between internal organs and bodily tissue during surgical procedures. First, the trocar obturator, which is the puncturing implement of the trocar assembly, is used to puncture the abdominal wall. The trocar obturator is subsequently removed, the abdomen is inflated, and the trocar cannula remains in place to provide access for surgical instruments to the surgical site. The cannula has a housing and a cannula tube extending from the housing. It is the housing which contains the seal. The housing also contains a valve, typically a flapper valve. When an instrument is inserted through the cannula, the instrument is inserted through the seal and causes the flapper valve to swing out of the way. The seal conforms to the outer diameter of the instrument, and therefore prevents the insufflation gas from exiting the body through the housing of the cannula. When the instrument is removed, the flapper valve automatically swings shut to likewise prevent insufflation gas from escaping.

One type of seal for a trocar is a simple gasket fixed to the cannula housing which has a diameter sized for the insertion and withdrawal of instruments of generally fixed diameter. Although simple in construction, it has the disadvantage of not being able to seal against instruments which have a diameter smaller that that for which the seal was sized. Accordingly, a reducer cap with a gasket diameter smaller than that of the housing to accommodate smaller sized instruments has been developed. The cap snaps onto the housing. Therefore, the surgeon can choose between the larger, fixed gasket of the housing or the smaller one on the reducer cap to ensure that an adequate seal around the instrument would be maintained when the instrument is inserted through the cannula. This reducer cap is described in U.S. Pat. No. 5,338,307.

While the reducer cap provides a greater degree of flexibility for inserting instruments with varying diameters through the cannula, it still requires the surgeon to manipulate the cap to provide the proper seal. Accordingly, efforts have been undertaken to develop an improved seal for a trocar.

A description of the first "universal seal" for a trocar is set forth in U.S. Pat. No. 5,395,342. The seal described in the '342 patent has an elastomeric cone with an aperture at its apex. The cone is fitted over a plurality of resilient legs extending from a frame fixed to the cannula housing. When an instrument is inserted through the seal, the instrument contacts the legs and causes them to expand against the elastomeric cone. This expansion facilitates the expansion of the aperture so it will conform to the outer diameter of the instrument. Significantly, the '342 patent provides the first description which inherently recognizes the less than desirable overall performance of seals composed of conventional elastomeric materials, such as silicone. Accordingly, it describes the use of resilient legs to facilitate the expansion of the seal, which is a key factor in the overall performance of the seal.

The recognition of the necessity of the legs to facilitate the expansion of a seal composed of a conventional elastomer manufactured using conventional techniques cannot be overstated. Without the legs, these elastomeric materials will not expand significantly. Therefore, if the aperture of the elastomeric seal is substantially smaller than the outer diameter of the instrument desired to be inserted through the cannula, the material surrounding the aperture may tear when the instrument is inserted. This, of course, is undesirable and may cause significant leakage of insufflation gas through the cannula.

In addition to the inability of conventional elastomers to provide the requisite degree of expansion, these conventional materials may not provide the required degree of tear resistance to prevent tearing of the seal when an instrument with a pointed tip contacts the outer periphery of the seal. This may occur when the surgeon is trying to insert the instrument through the seal aperture, and misguides the tip so that it contacts the outer periphery instead of the centrally located aperture. The lack of tear resistance has led to the development of seal designs to protect the elastomeric seal during instrument insertion. For example, U.S. Pat. No. 5,342,315 describes the use of "protectors" surrounding the elastomeric seal which come into direct contact with the instrument during instrument insertion. The protectors prevent direct contact of the instrument tip with the elastomeric seal, and therefore significantly minimize or prevent the instrument tip from tearing the outer periphery of the seal. Another protector configuration designed to isolate the instrument from the outer periphery of the elastomeric seal is described in U.S. Pat. No. 5,308,336.

Although universal seals for trocars have been developed to provide a seal against instruments of varying diameters, none of these seals is capable of overcoming the substantial deficiencies inherent in the use of conventional elastomeric materials which are suitable for surgical applications. Therefore, these seals have required the use of additional seal components such as resilient legs or protectors to overcome these material deficiencies. Unfortunately, these additional components add cost, manufacturing complexity and reduced reliability to the overall seal design. It would be highly desirable, in view of this ongoing deficiency, to develop a universal seal for a trocar which does not require the use of resilient legs or protectors to compensate for inadequacies of conventional elastomeric materials adapted for surgical applications.

SUMMARY OF THE INVENTION

The invention is a trocar for providing access for insertion and withdrawal of surgical instruments to and from a surgical site within a body cavity. The trocar comprises a trocar cannula and a seal assembly.

The trocar cannula has a cannula housing and a tubular sleeve extending from the housing. The cannula housing has a passageway communicating with the sleeve. The passageway creates a path through the cannula for providing the access for insertion and withdrawal of the surgical instruments.

The seal assembly is fixed to the cannula housing in the path of the passageway communicating through the trocar cannula. The seal assembly includes a seal composed of an elastomeric material for sealing against the surgical instruments having varying diameters. The seal has a centrally located interior region containing an aperture. A sealing region is concentrically located about the interior region of the seal. The sealing region comprises an integral laminate which is co-molded from the elastomeric material. The laminate has a first underlying layer and a second overlaying layer. The first underlying layer has a Shore A Durometer hardness between about 5 and about 40. The second overlaying layer has a hardness between about 40 Shore A Durometer and about 80 Shore D Durometer.

Significantly, the second overlaying layer which is co-molded with the first underlying layer to make the integral laminate of the sealing region of the seal assembly eliminates the need to incorporate resilient legs or protectors into the seal assembly. The second overlaying layer has a hardness greater than that of the first underlying layer. Therefore, the contact area and the frictional force between an instrument as it is inserted through the cannula and the second overlaying layer is much less than it would be if it were in direct contact with the underlying layer. In addition, the second overlaying layer has greater resistance to tearing when it comes into contact with the inserted instrument. Correspondingly, the first underlying layer has greater elasticity than the second overlaying layer, and consequently facilitates the stretching of the aperture in the interior region of the seal assembly when an instrument having a diameter greater than that of the aperture is inserted through the cannula. The seal balances the need for tear resistance on the surface contacting the instrument with elasticity to facilitate the stretching of the aperture without ripping during insertion. As a result, the need for costly additional components for the seal assembly to enhance tear resistance or elasticity of the seal, such as resilient legs and protectors, is avoided.

Furthermore, the sealing region of the seal assembly of the trocar of this invention enables smooth withdrawal of instruments from the trocar cannula without catching or snagging onto the seal assembly as the instruments are withdrawn. This is because the seal assembly does not need to incorporate additional components projecting into the sealing region. Therefore, damage to the seal assembly is minimized. Additionally, the sealing region will readily evert when instruments are withdrawn because the second overlaying layer exhibits increased stiffness. This too decreases the chance for damage to the seal assembly. Finally, the ability to remove tissue specimens from the body through the trocar cannula is enhanced because additional seal components are unnecessary which would obstruct the cannula passageway.

The elastomeric seal of the seal assembly can be configured in numerous shapes. For example, the seal can be flat or conical. Preferably, the second overlaying layer of the sealing region can be displayed as a plurality of separate or interconnected concentric plates on top of the first underlying layer. Most preferably, the second overlaying layer is a plurality of separate plates on top of the first underlying layer. In this embodiment, when an instrument is inserted through the seal assembly, the segmented nature of the overlaying layer minimizes its deformation while the underlying layer between the separate plates, specifically chosen for its ability to deform, accepts the deformation. In effect, the underlying layer in this preferred embodiment actually affords protection of the overlaying layer.

Alternatively, the second overlaying layer may be a continuous layer co-molded on top of the first underlying layer.

The trocar of this invention has a seal assembly which seals against surgical instruments of varying diameters to maintain insufflation in the body cavity during endoscopic surgery. As of the filing date of this application, surgical instruments with diameters between 5–12 mm have conventionally been used during endoscopic surgery. Consequently, the seal assembly of the trocar of this invention can accommodate the insertion and withdrawal of instruments with diameters in this range. In the current invention, the seal assembly can accommodate instruments within a wider or narrower range of diameters.

The trocar of this invention can be used in all of the surgical procedures where trocars have conventionally been used or contemplated for use. Of course, the trocar of this invention is particularly adapted for endoscopic applications where it is necessary to insert instruments of varying diameter through the trocar while still maintaining insufflation within the body cavity.

DETAILED DESCRIPTION OF THE PREFERRED EMBODIMENTS

Figure 1:
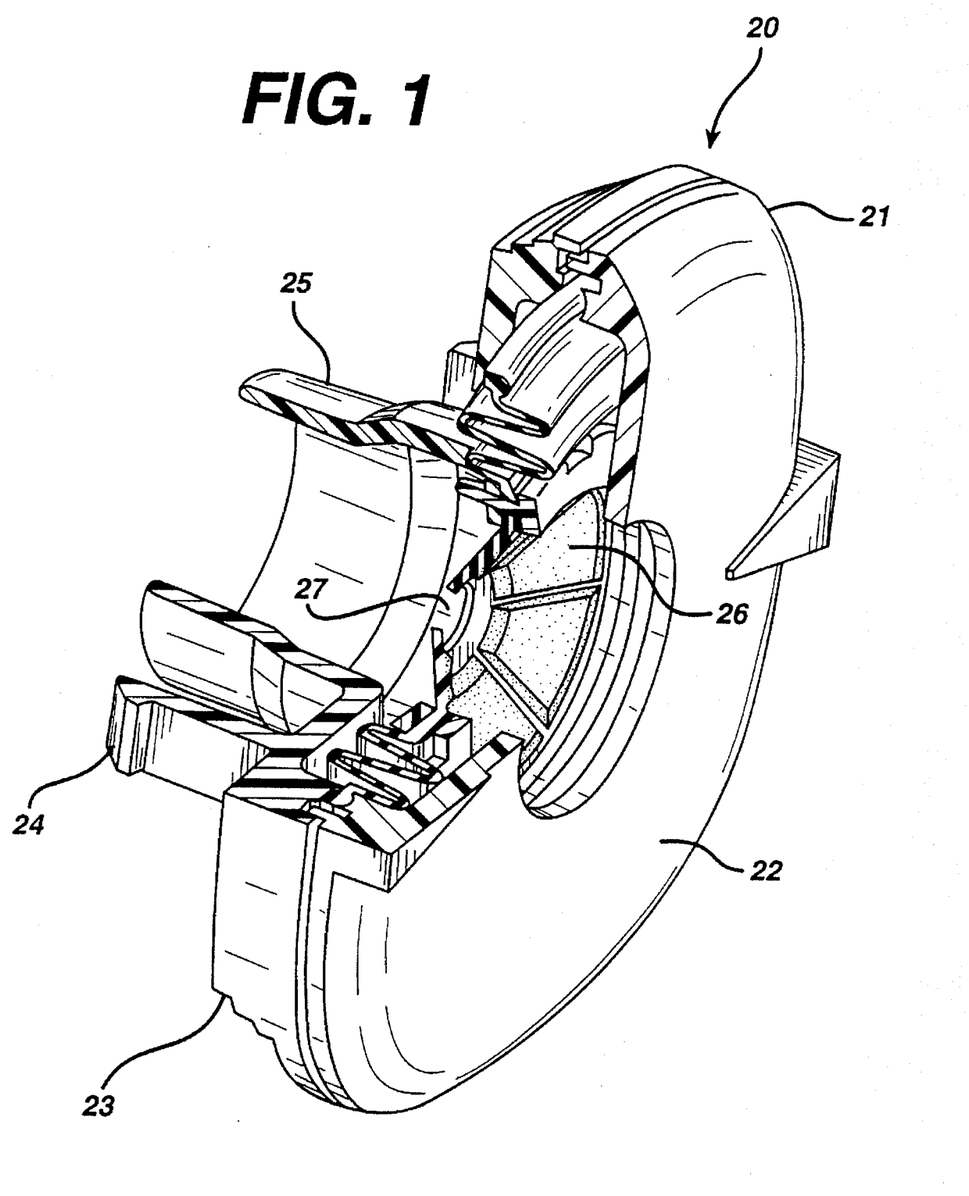
FIG. 1 is a perspective view of the seal assembly of the trocar of this invention shown in partial cross-section.

A preferred seal assembly 20 for the trocar of this invention is illustrated in FIG. 1. The seal assembly is an integrated unit which is designed to snap onto the housing of the trocar cannula. It has a frame 21 which is sized to fit over the top of the cannula housing. The frame has an exterior planar face 22 and an interior region 23 which is positioned within the cannula housing. The interior region includes a resilient latches 24 which secures the seal assembly to the housing. It also includes a neck 25 to facilitate the guidance of surgical instruments through the cannula as they are inserted into and withdrawn from the cannula, and to seal the assembly 20 against the outer gasket of the trocar to prevent the escape of gas around the frame 21.

The seal assembly depicted in FIG. 1 has an elastomeric seal 26 to seal against instruments which are inserted into and withdrawn from the cannula. The seal is positioned centrally within the seal assembly. The seal includes a centrally positioned aperture 27 to permit the passage of the instruments. Advantageously, the aperture has a diameter between about 2.5 to about 5 mm so it can seal not only against the smallest endoscopic instruments but also 12 mm instruments and larger ones as well.

Figure 2:
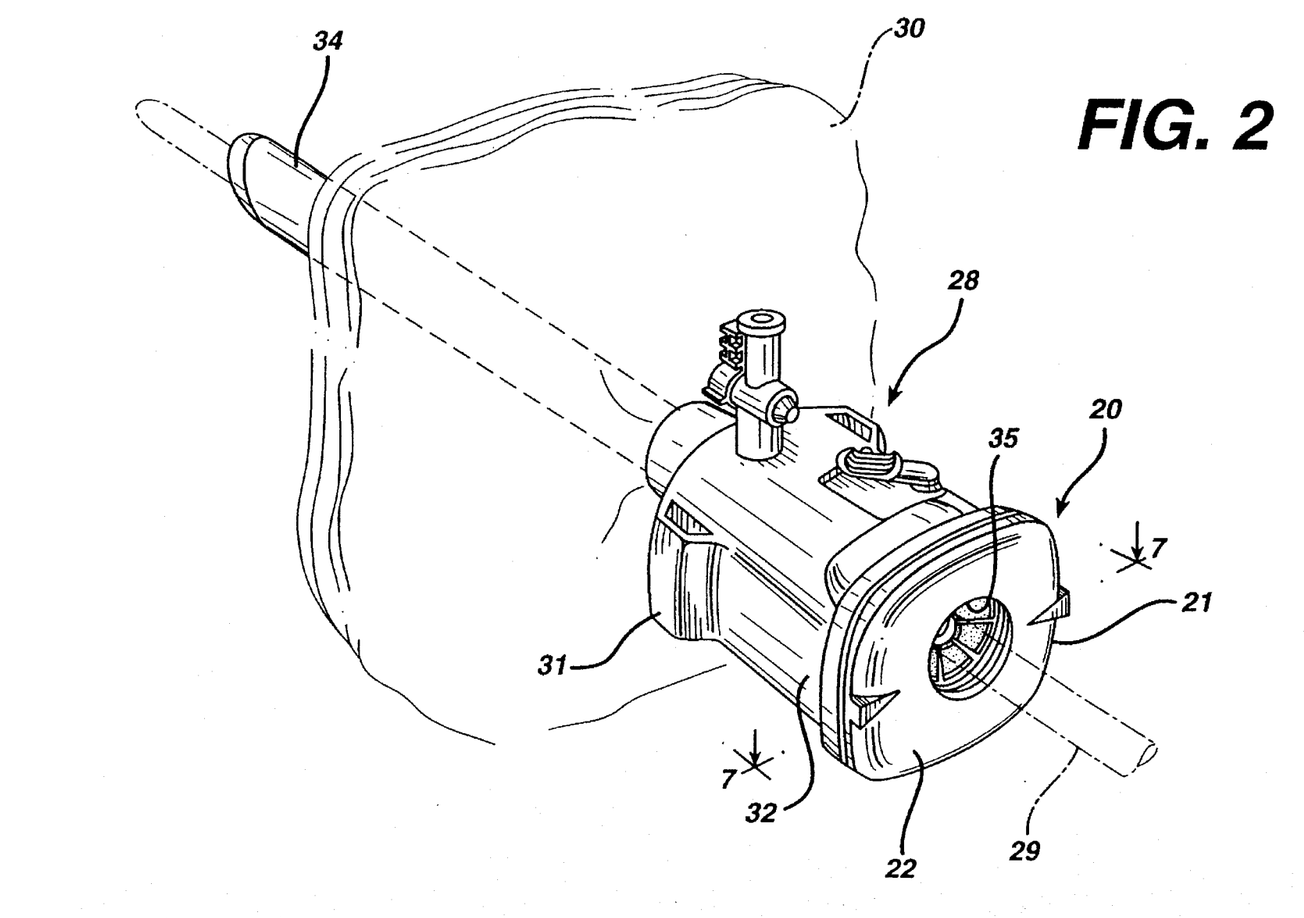
FIG. 2 is a perspective view of the trocar providing access for a surgical instrument within a body cavity, where the seal assembly illustrated in FIG. 1 is attached to the trocar.

Referring to FIG. 2, the trocar 28 of this invention is seen to provide access for the insertion for a surgical instrument 29 into a body cavity. The body wall 30 of the surgical patient is punctured with the trocar obturator (not shown), and the obturator is subsequently withdrawn from the cannula 31. The cannula has a housing 32 with an interior chamber 33 (see FIGS. 7 and 8), and an elongated, cylindrical sleeve 34 extending from the housing. The sleeve extends through the opening made in the body wall. At the proximal end of the cannula housing, the seal assembly 20 is secured. A passageway 35 is provided through the aperture of the seal assembly, into the chamber of the cannula housing, and finally through the lumen of the tubular sleeve to provide a path for the insertion and withdrawal of a surgical instrument into the body cavity.

Figure 3:
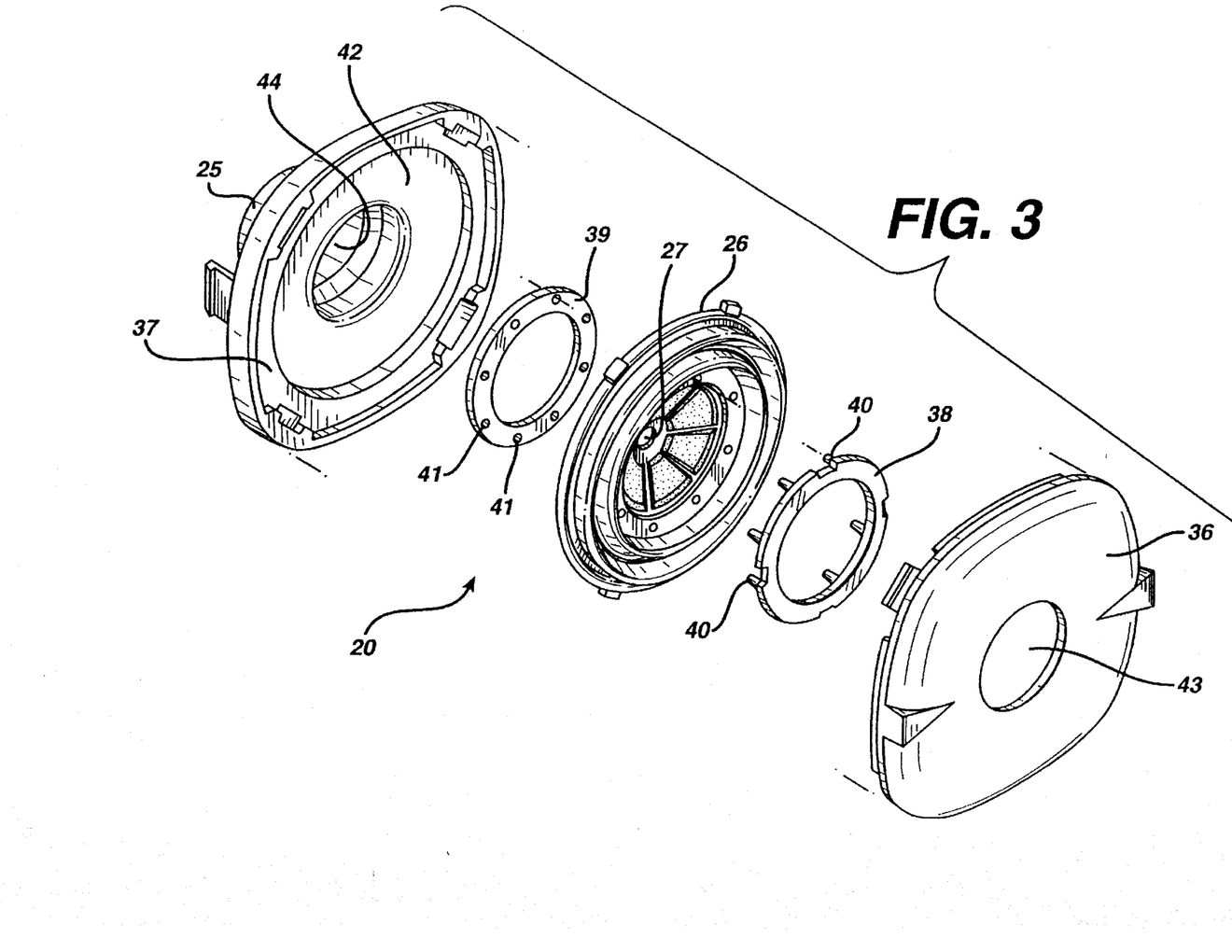
FIG. 3 is an exploded perspective view of the seal assembly illustrated in FIG. 1.

The components of the preferred seal assembly 20 are illustrated in FIG. 3. The frame is a subassembly which has a top frame half 36 and a bottom frame half 37. Sandwiched between the top and bottom frame halves is the elastomeric seal 26. The seal is positioned between upper and lower rigid rings, 38 and 39, respectively. The upper ring has a plurality of prongs 40 which are fitted through the seal and are received in a plurality of receiving holes 41 in the lower ring. The top and bottom frame halves define an internal cavity 42 for receiving the seal 26. The top frame half has a circular opening 43 sized to fit an instrument with the largest diameter contemplated. Correspondingly, the bottom frame half has a similarly sized opening 44 which is funneled to form the neck 25 of the seal assembly. A detailed description of a seal assembly with similar components is described in U.S. Pat. No. 5,342,315.

Figure 4:
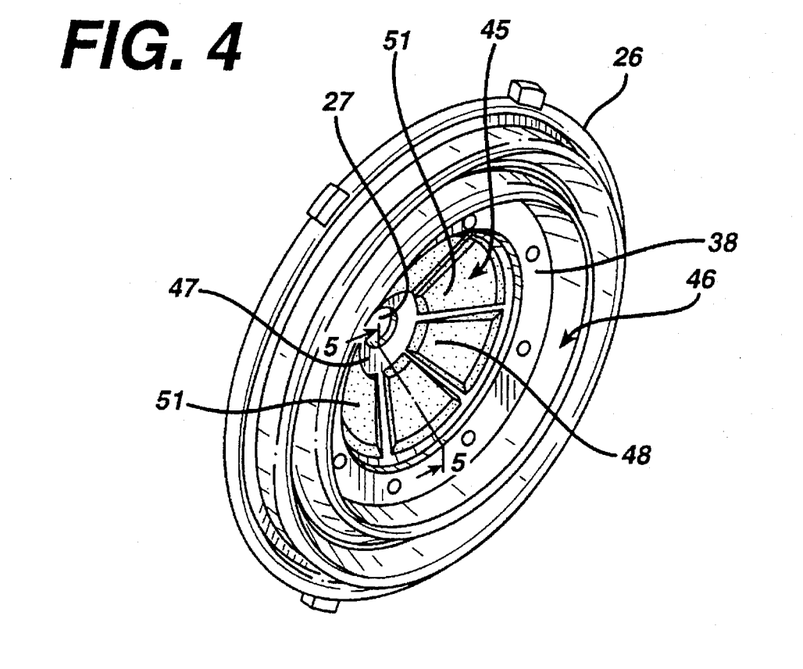
FIG. 4 is a perspective view of the elastomeric seal component of the seal assembly illustrated in FIG. 1.
Figure 5:
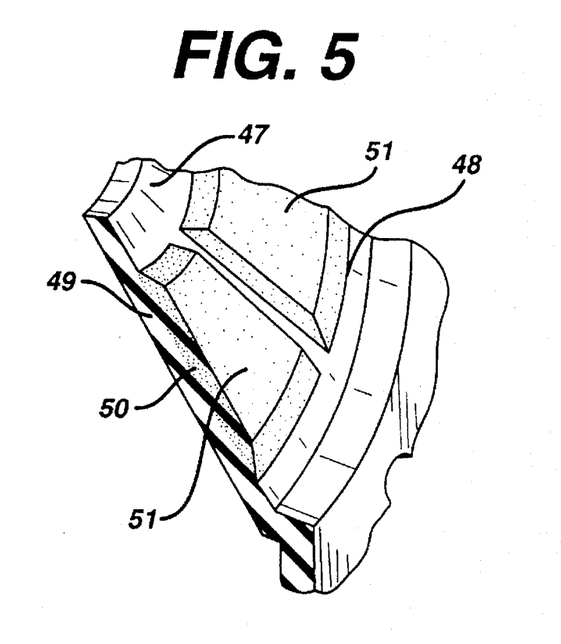
FIG. 5 is a fragmentary perspective view in partial cross-section of the elastomeric seal component as seen along view line 5—5 of FIG. 4.
Figure 6:
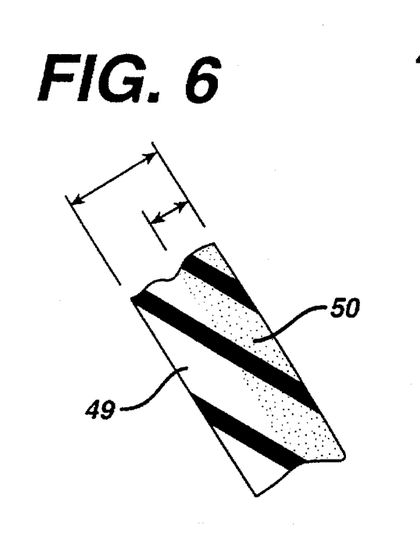
FIG. 6 is an enlarged fragmentary view of the elastomeric seal component shown in FIGS. 4 and 5.

Referring now to FIGS. 4-6, the seal component 26 of the preferred seal assembly is illustrated. The seal is made of a medical grade elastomer. Examples of suitable elastomers include, but are not limited to, silicone rubber, polyurethane elastomer, chlorobutyl rubber, latex rubber, polyisoprene rubber and ethylene propylene diene monomer ("EPDM") rubber. The preferred elastomer are silicone rubber and polyurethane rubber. The most preferred elastomer is medical grade silicone, for example, Dow Corning Slastic™ brand medical grade silicone rubber.

The seal has inner and outer portions, 45 and 46, respectively. The inner and outer portions are divided by the upper and lower rigid rings. The outer portion of the seal has a bellows configuration. As disclosed in U.S. Pat. Nos. 5,073,169 and 5,209,736, the bellows facilitates the maintenance of a seal during radial motion of surgical instruments which are inserted into and withdrawn from the cannula. The inner portion of the seal has a centrally located interior region 47 which contains the aperture 27 for passage of the surgical instruments. The circumferential surface of the aperture seals against instruments because it provides the surface against which the instruments come into contact. A sealing region 48 is concentrically located about the interior region of the seal. It is this sealing region which supports the aperture 27 of the interior region of the seal assembly when instruments are inserted and withdrawn, and prevents or minimizes the escape of insufflation gas from the body cavity through the trocar cannula. Accordingly, the seal region must have the dual properties of elasticity to enable the passage of large instruments through the aperture 27, and toughness to prevent ripping when misaligned instruments are forced against the sealing region.

Significantly, the sealing region has two layers. It has a first underlying layer 49 located interiorly towards the surgical patient, and a second overlaying layer 50 positioned on top of the first layer. The two layers are integral with each other to create an integral laminate. The laminate of the elastomer can be made using conventional injection co-molding techniques which are well known in the art. In other words, the first underlying layer of the elastomer is initially molded, and then the second overlaying layer of the elastomer is subsequently molded on top of the first layer to create the integral laminate. The underlying layer is elastic so that the aperture will stretch in response to instrument insertion, and the overlaying layer is tear resistant to prevent ripping. Accordingly, the tear resistance of the overlaying layer is advantageously greater than that of the underlying layer.

Generally, the specific tear strength chosen for the underlying and overlaying layers will depend on the degree of resistance to seal tearing desired, which correspondingly depends on the size of surgical instruments inserted into and withdrawn from the trocar cannula and the shape of the end effectors of these instruments. In addition, the tear strength will also depend on the particular configuration of the elastomeric seal. For example, a seal which has a configuration with a large surface area to facilitate expansion of the seal aperture may need less tear strength than a seal with a configuration with a small surface area. Therefore, the specific hardness for the underlying and overlaying layers may be readily determined empirically. Nevertheless, the first underlying layer of the elastomer in the sealing region of the sealing assembly preferably has a hardness between about 5 Shore A Durometer Scale and about 40 Shore A Durometer Scale. The second overlaying layer has a hardness which is preferably between about 40 Shore A Durometer Scale and about 80 Shore D Durometer Scale. The hardness of the elastomer can be determined using the standard test method for hardness of the thermoplastic elastomers set forth in ASTM D 2240-91.

Overall, if the hardness of the first underlying layer is less than about 5 Shore A Durometer Scale, then the underlying layer may become very adherent or "sticky" to the instrument inserted through the seal assembly, consequently causing high friction and leading to the possible tearing of the seal assembly. Correspondingly, if the hardness of the first underlying layer is greater than about 40 Shore A Durometer Scale, then the underlying layer becomes increasingly stiff, minimizing the flexibility or elongation of the layer which may cause the possible tearing of the layer or an increase in instrument insertion force. If the second overlaying layer has a hardness less than about 40 Shore A Durometer Scale, then there is the potential for increased friction and surface contact between the instrument and the seal which may cause tearing of the seal assembly. Correspondingly, if the second overlaying layer has a hardness greater than about 80 Shore D Durometer Scale, then there is the potential for the shearing of the first underlying layer upon instrument withdrawal which may cause tearing of the seal assembly. Also, a hardness greater than 80 Shore D Durometer Scale minimizes the elastic flexibility of the overlaying layer, thus potentially inhibiting tissue removal and causing instrument snags. Preferably, the first underlying layer of the sealing region of the sealing assembly has a hardness between about 30 Shore A Durometer Scale and about 40 Shore A Durometer Scale. The second overlaying layer of the sealing region preferably has a tear resistance between about 50 Shore A Durometer Scale and about 80 Shore D Durometer Scale. Most preferably, the second overlaying layer has a tear resistance between about 60 Shore A Durometer Scale and about 70 Shore A Durometer Scale.

The sealing region of the seal assembly depicted in FIGS. 4-6 is configured as a shallow cone. The overlaying layer of the co-molded integrate laminate is displayed as a plurality of separate concentric plates 51 in the form of truncated triangles.

Figure 7:
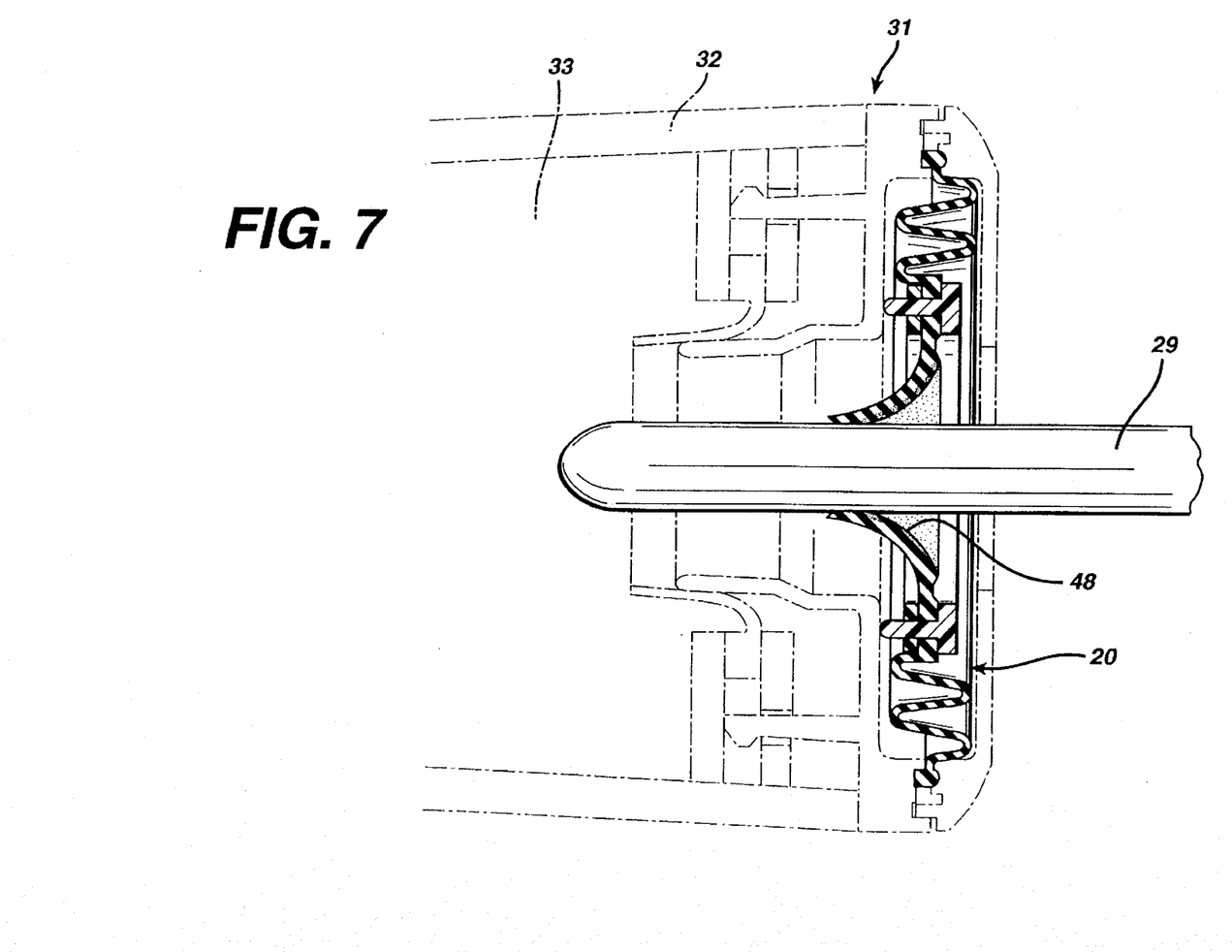
FIG. 7 is a schematic top plan view of the seal assembly sealing against a surgical instrument as seen along view line 7—7 of FIG. 2.
Figure 8:
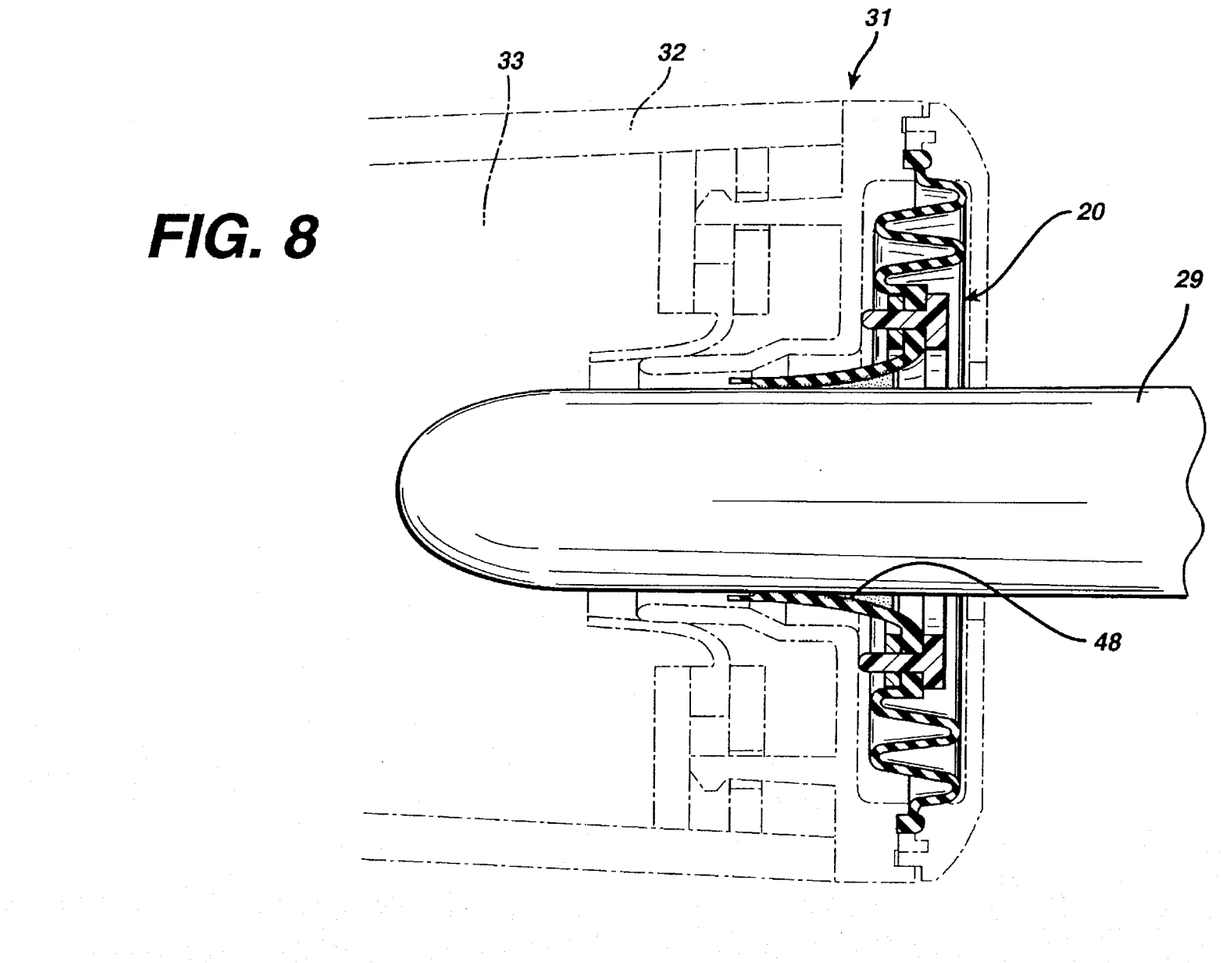
FIG. 8 is a view similar to FIG. 7 in which the instrument is of a larger diameter.

FIGS. 7 and 8 depict the insertion of surgical instruments of varying diameter through the trocar cannula 31, and the seal which is created between the instrument 29 and the sealing region 48 of the seal assembly 30. As the instrument is inserted through the aperture of the seal, the aperture expands to accommodate the outside diameter of the instrument inserted through the seal.

Figure 9:
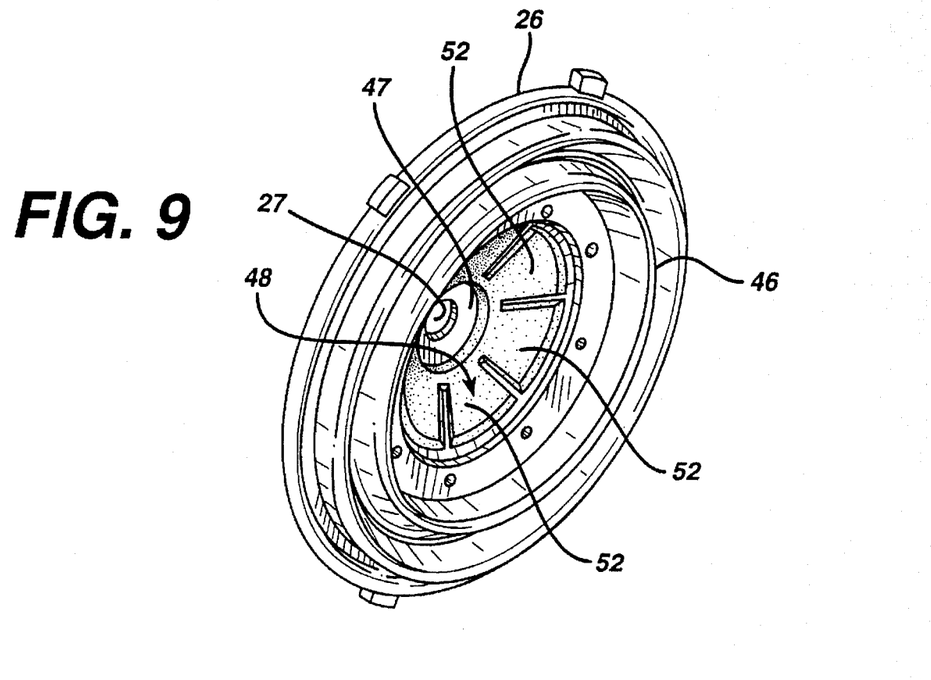
FIGS. 9–15 are perspective views of alternate embodiments for the seal assembly of the trocar of this invention.
Figure 10:
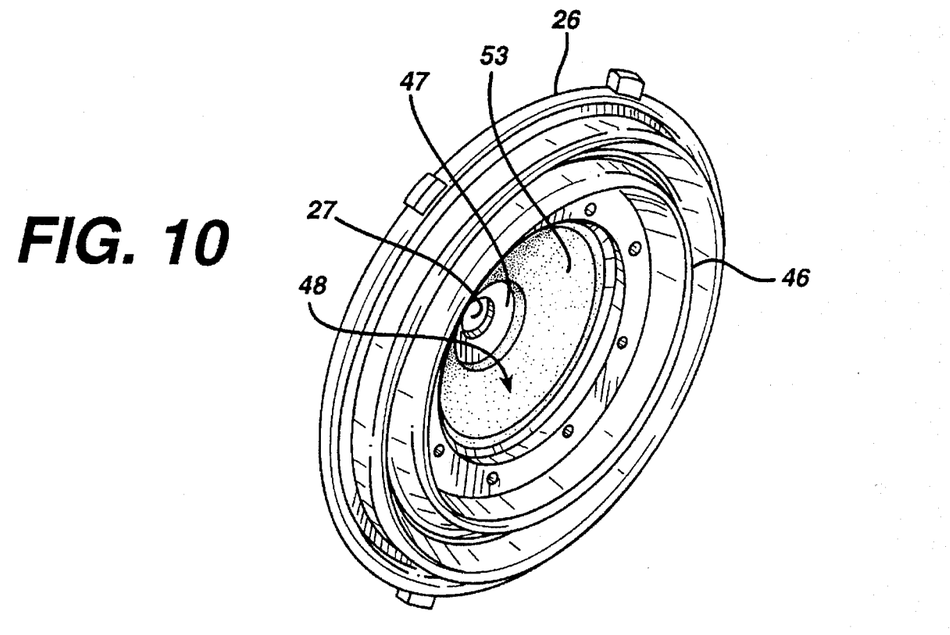
Figures 11, 12, 13:
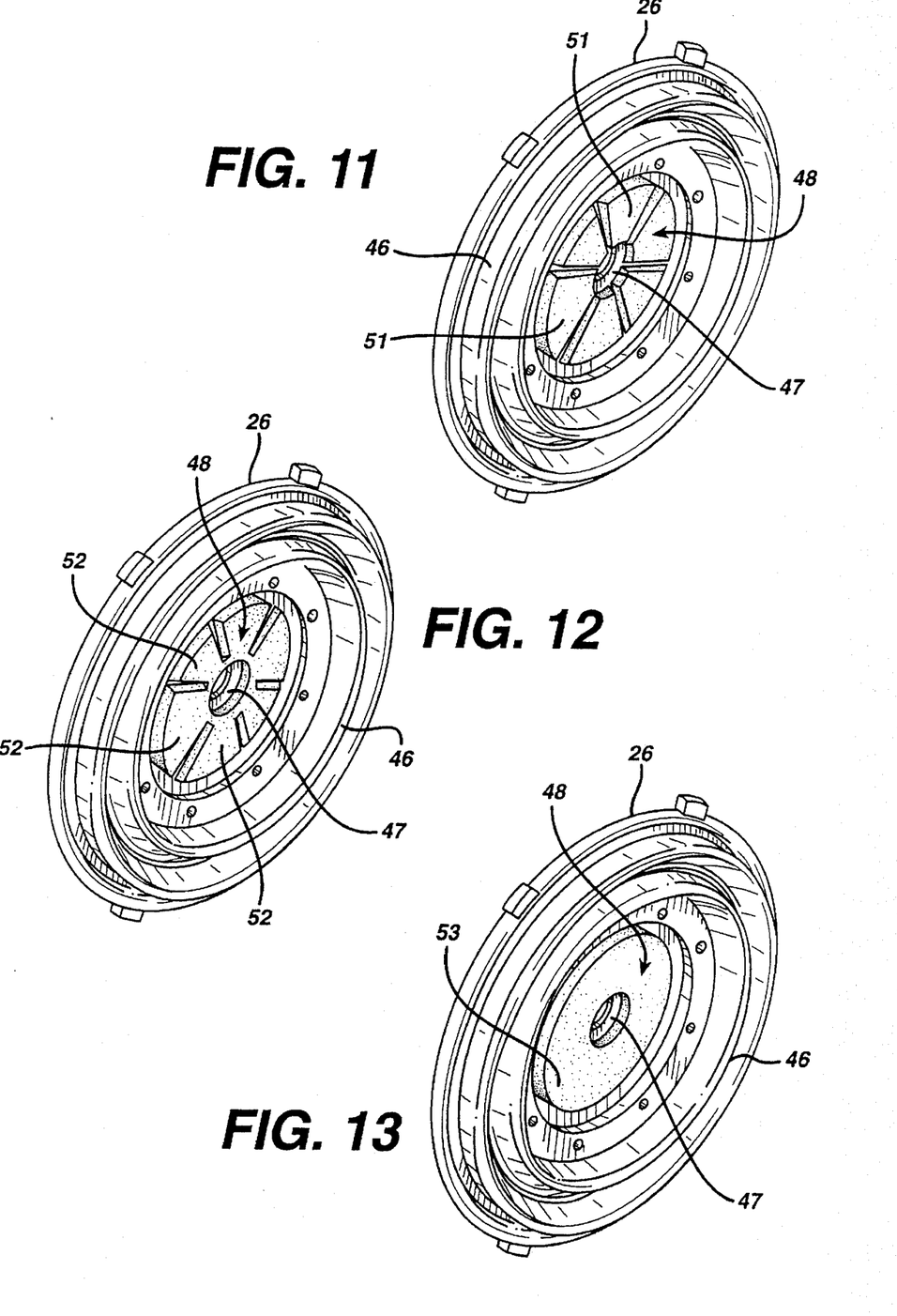
Figure 14:
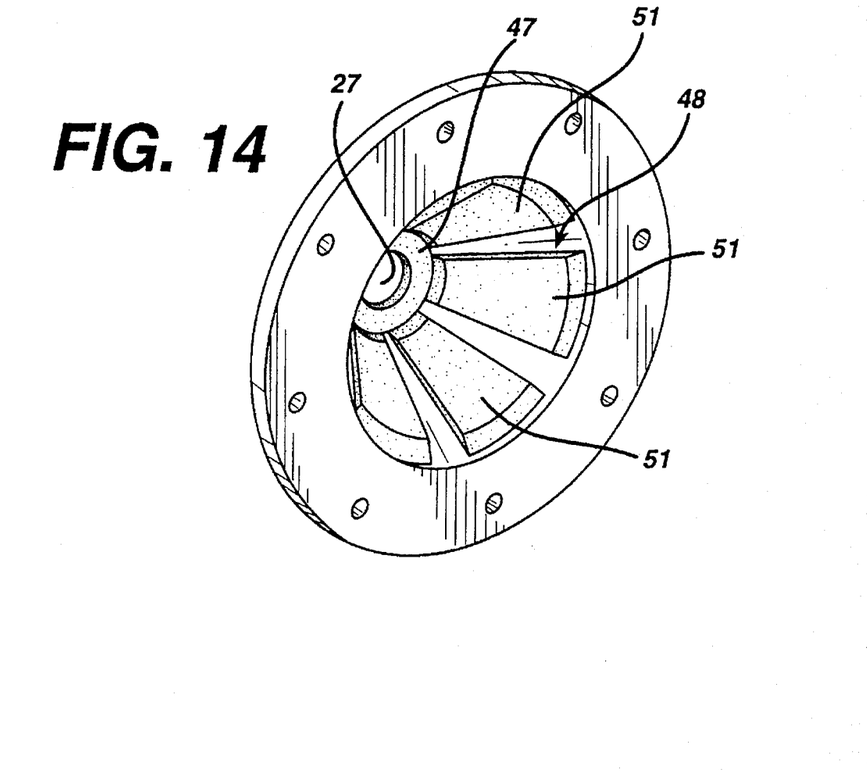
Figure 15:
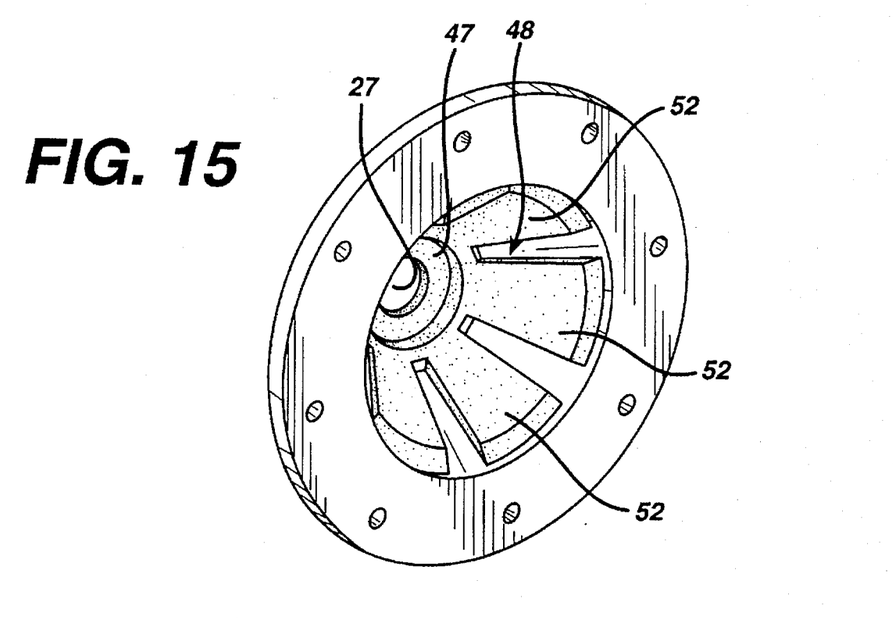

Referring briefly now to FIGS. 9–15, there are illustrated alternative embodiments for the configuration of the seal component 26 of the seal assembly for the trocar of this invention. FIG. 9 depicts a second overlaying layer of the sealing region 48 as a plurality of interconnected concentric plates 52. FIG. 10 illustrates the second overlaying layer region of the sealing region as a continuous layer 53 co-molded over substantially the entire surface of the underlying layer. In FIGS. 11–13, the sealing region of the seal assembly is configured as a flat seal instead of a shallow cone. Alternatively, the sealing region can be configured as a deep cone as shown in FIGS. 14 and 15. In the embodiments of FIGS. 14 and 15, the outer portion 46 of the seal depicted in FIGS. 4 and 9–13 have been eliminated.

In another embodiment of this invention, the seal assembly may be insert molded directly to the interior wall of the cannula housing of the trocar instead of the latch attachment illustrated in FIGS. 1 and 2. For example, the cannula housing can be initially inserted into a mold. The first underlying layer of the sealing region of the seal assembly can be injected into the mold to form the outer perimeter of the seal as well as to form a mechanical interlock with the cannula housing. Subsequently, the second overlaying layer may be co-injected into the mold. Once the elastomer is fully cured, the cannula housing can be demolded.

Although this invention has been described in connection with its most preferred embodiments, numerous additional embodiments can readily be contemplated by those skilled in the art and therefore fall within the scope and spirit of the claimed invention. The detailed description of the preferred embodiments are exemplary only, and should not be construed in any way to limit the scope of the claimed invention.

What is claimed is:

1. A trocar for providing access for insertion and withdrawal of surgical instruments to and from a surgical site within a body cavity, said trocar comprising:

a) a trocar cannula, said cannula having a cannula housing and a tubular sleeve extending therefrom, said cannula housing having a passageway communicating with said sleeve so as to create a path through said cannula for providing access for insertion and withdrawal of said surgical instruments; and b) a seal assembly affixed to said cannula housing in said path of said passageway, said seal assembly including a seal composed of an elastomeric material for sealing against said surgical instruments of varying diameter, said seal having a centrally located interior region containing an aperture therethrough, and a concentrically located sealing region, wherein said sealing region comprises an integral laminate co-molded from said elastomeric material, said laminate having a first underlying layer and a second overlaying layer, said first underlying layer having a hardness between about 5 Shore A Durometer Scale and about 40 Shore A Durometer Scale, and said second overlaying layer having a hardness between about 40 Shore A Durometer Scale and about 80 Shore D Durometer Scale.

2. The trocar of claim 1 wherein said elastomeric material is selected from the group consisting of silicone robber, polyurethane elastomer, chlorobutyl rubber, polyisoprene rubber and ethylene propylene diene monomer ("EPDM") rubber.

3. The trocar of claim 2 wherein said elastomeric material is polyurethane or silicone rubber.

4. The trocar of claim 3 wherein said elastomeric material is silicone rubber.

5. The trocar of claim 1 wherein said first underlying layer of said sealing region has a tear strength between about 30 Shore A Durometer Scale and about 40 Shore A Durometer Scale.

6. The trocar of claim 5 wherein said second overlaying layer of said sealing region has a tear resistance between about 60 Shore A Durometer Scale and about 70 Shore D Durometer Scale.

7. The trocar of claim 1 wherein said second overlaying layer of said sealing region is displayed as a plurality of separate concentric plates.

8. The trocar of claim 1 wherein said second overlaying layer of said sealing region is displayed as a plurality of interconnected concentric plates.

9. The trocar of claim 1 wherein said second overlaying layer of said sealing region is a continuous layer co-molded over substantially the entire surface of said first underlying layer.

10. The trocar of claim 1 wherein said seal is generally a flat seal.

11. The trocar of claim 1 wherein said seal is a conical seal.

* * * * *